(12) United States Patent
Chen

(10) Patent No.: US 6,233,495 B1
(45) Date of Patent: May 15, 2001

(54) METHODS FOR MODELING TWO-DIMENSIONAL RESPONSES OF CROSS-MACHINE DIRECTION ACTUATORS IN SHEET-FORMING PROCESSES

(75) Inventor: Shih-Chin Chen, Dublin, OH (US)

(73) Assignee: ABB Automation, Inc., Columbus, OH (US)

( * ) Notice: Subject to any disclaimer, the term of this patent is extended or adjusted under 35 U.S.C. 154(b) by 0 days.

(21) Appl. No.: 09/096,622

(22) Filed: Jun. 12, 1998

(51) Int. Cl.[7] .............................. G06F 19/00; G05B 13/02
(52) U.S. Cl. .............................. 700/122; 700/29; 700/31; 700/38; 700/128; 700/129
(58) Field of Search ................................ 700/29, 30, 31, 700/38, 39, 122, 128, 129, 127, 44; 702/170, 179

(56) References Cited

U.S. PATENT DOCUMENTS

| | | | |
|---|---|---|---|
| 4,451,878 | 5/1984 | Shigemasa | 700/31 |
| 5,122,963 | 6/1992 | Chen | 700/129 |
| 5,400,258 | 3/1995 | He | 700/129 |
| 5,470,005 | 11/1995 | King et al. | 226/1 |
| 5,539,634 | 7/1996 | He | 700/38 |
| 5,715,158 | * 2/1998 | Chen | 700/30 |
| 5,893,055 | * 4/1999 | Chen | 702/189 |
| 6,086,237 | * 7/2000 | Gorinevsky et al. | 700/127 |

FOREIGN PATENT DOCUMENTS

| | | |
|---|---|---|
| 0 334 698 | 1/1989 | (EP) . |
| WO 91/05105 | 4/1991 | (WO) . |

\* cited by examiner

*Primary Examiner*—William Grant
*Assistant Examiner*—Paul Rodriquez

(74) *Attorney, Agent, or Firm*—King & Schickli PLLC

(57) ABSTRACT

A plurality of random probing sequences are used to perturb a corresponding plurality of cross-machine direction (CD) actuators of a web manufacturing machine. The web of sheet material is measured as the CD actuators are perturbed. The global process machine direction (MD) dynamics is estimated and a CD response is estimated for each of the plurality of CD actuators using the plurality of random probing sequences, measurements of the web of sheet material and the estimated global process MD dynamics. The estimated global process MD dynamics and the estimated CD responses form 2D responses for the plurality of CD actuators. To refine the 2D responses, the estimates of global process MD dynamics, and CD responses for each of the plurality of CD actuators are iterated. The actuator dynamics of the plurality of CD actuators may also be estimated and used in the estimates of the global process MD dynamics of the plurality of CD actuators and CD responses for each of the plurality of CD actuators. Variations that are not associated with actuator responses are removed from the estimated CD responses, for example by filtering. The estimated CD responses may be further refined by selecting one of the CD responses as a reference response. All remaining CD responses are shifted into alignment with the reference response to determine relative CD response locations and to define a group of overlapping CD responses. Using iterative techniques, a mean response is determined from a group of overlapping CD responses and variation bounds are set above and below the mean response. A family of probable CD responses are generated within the variation bounds and a most probable response is selected from the family of probable responses for each CD actuator response. The CD response for each CD actuator is replaced with the most probable response shifted by an appropriate amount for each CD actuator and multiplied by an optimal gain.

20 Claims, 13 Drawing Sheets

(5 of 13 Drawing Sheet(s) Filed in Color)

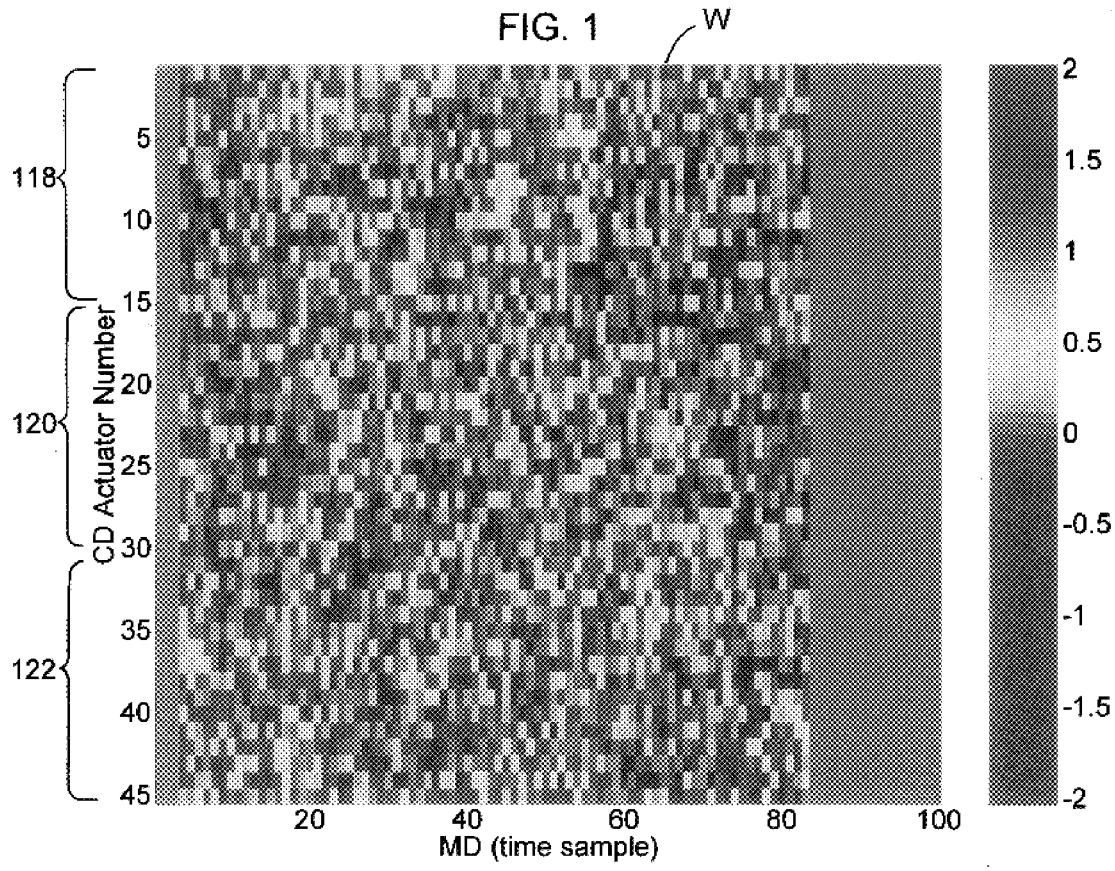

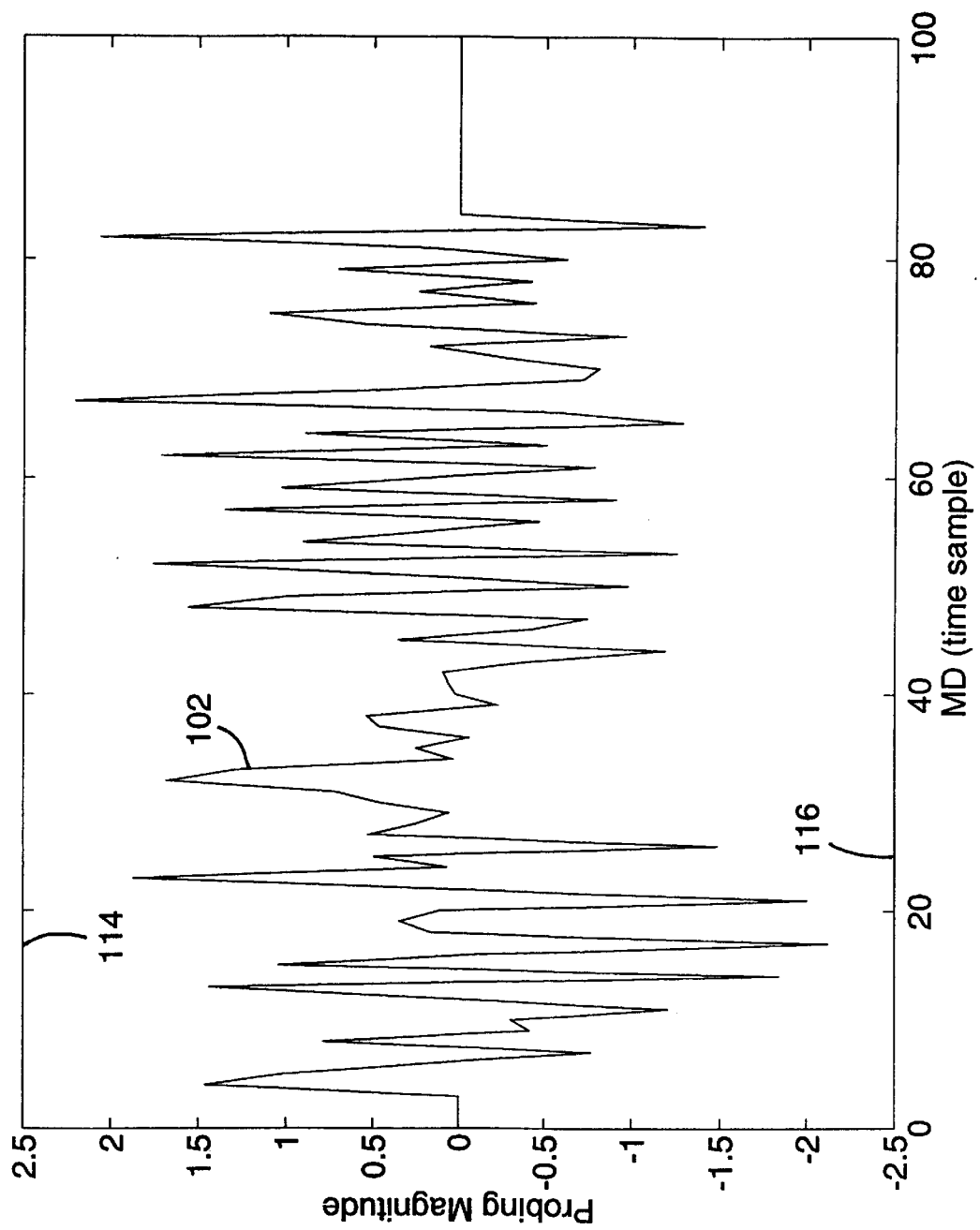

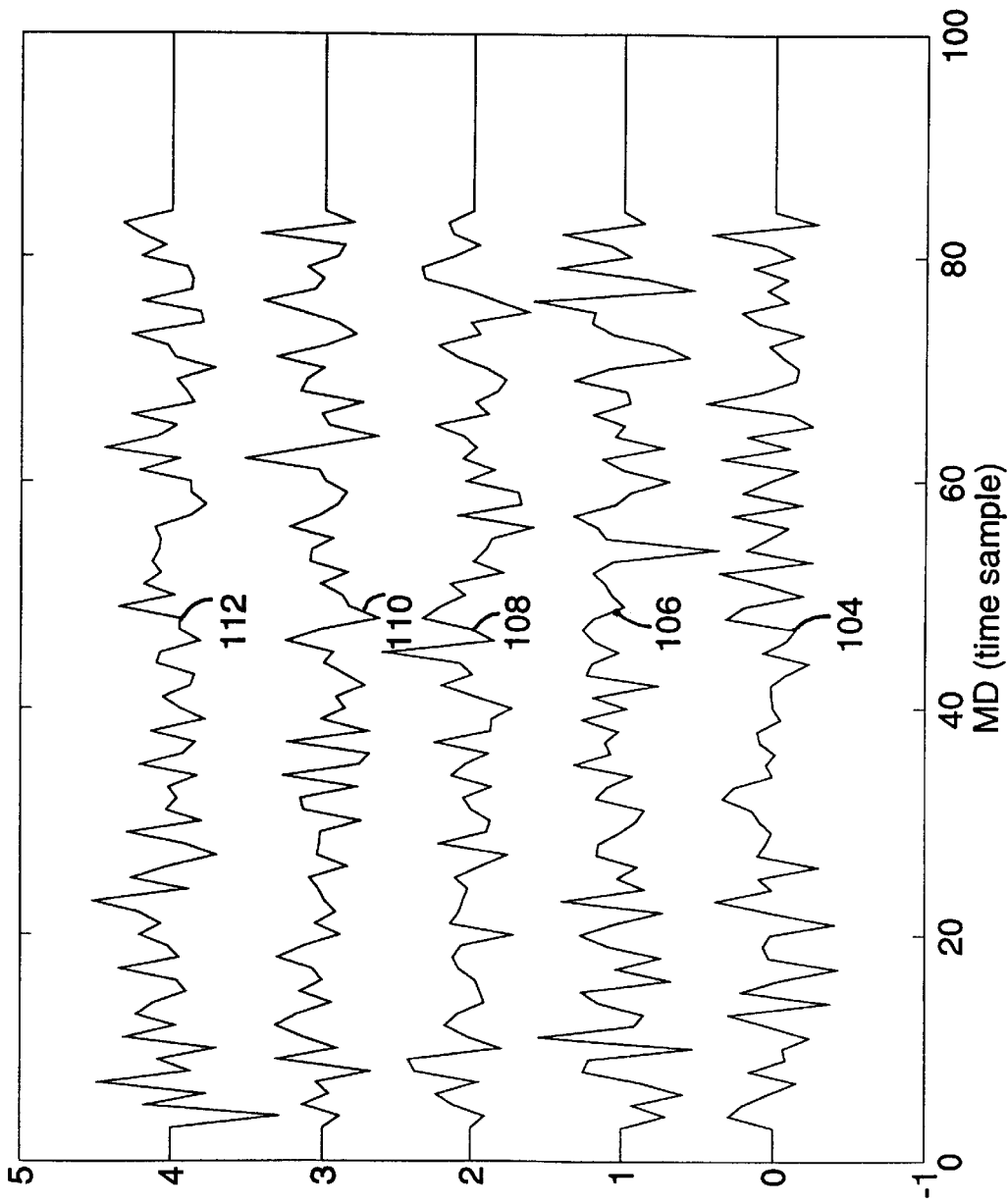

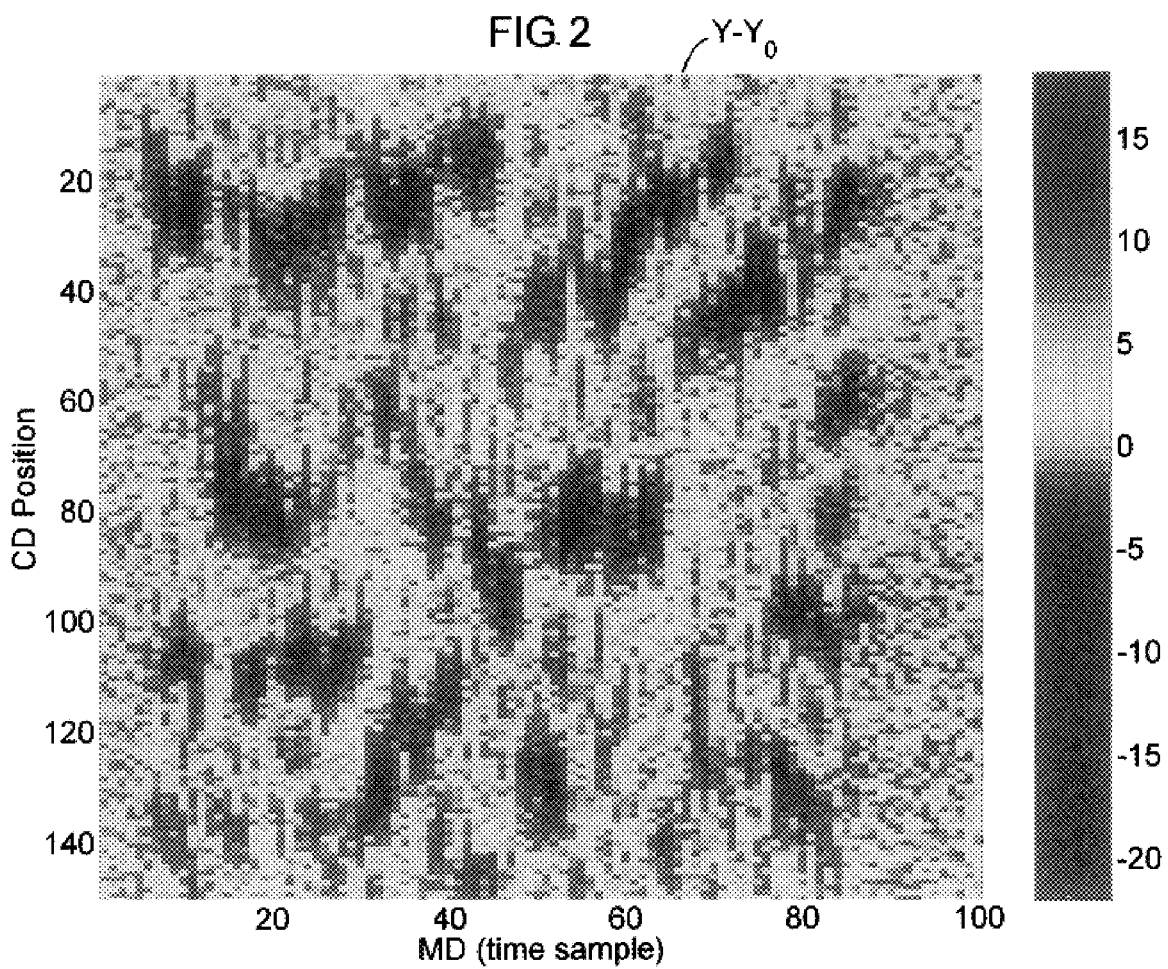

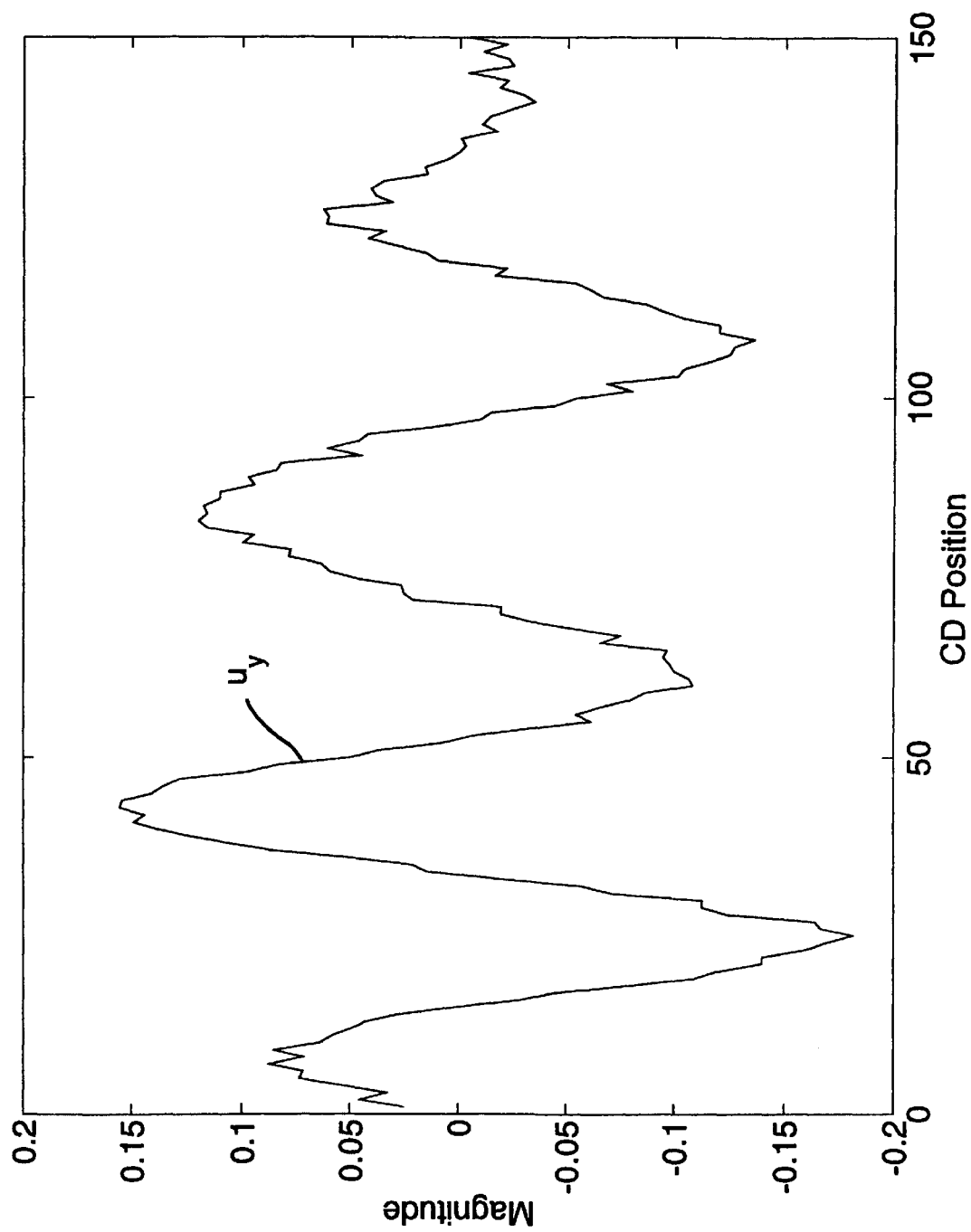

METHODS FOR MODELING TWO-DIMENSIONAL RESPONSES OF CROSS-MACHINE DIRECTION ACTUATORS IN SHEET-FORMING PROCESSES

BACKGROUND OF THE INVENTION

The present invention relates in general to processes for forming webs of sheet material and, more particularly, to methods for quickly determining accurate models to characterize the two-dimensional responses of cross-machine direction (CD) actuators used to control the operation of such web forming machines.

Many sheet-forming processes such as paper machines, plastic film extruders, super-calenders, coaters, and similar processes face common process control problems in producing webs which satisfy specifications for the given sheet material. Web specifications commonly include ranges for characteristics of the web including thickness, moisture content, weight per unit area and the like. Quality control is complicated since the specified characteristics vary in both the machine direction (MD) or direction of movement of the web through the machine and also in the cross-machine direction (CD) or laterally across the web.

The MD variations are generally affected by factors that impact the entire width of the web, such as machine speed, the source of base material being formed into a web by the machine, common supplies of working fluids like steam, and similar factors. CD variations, represented by profiles or profile signals, are normally controlled by arrays of actuators distributed across the width of the machine. On paper making machines, for which the present invention is particularly applicable, the CD actuators include basis weight actuators which control the slice of a headbox and/or headbox dilution valves, steam shower nozzles, infrared heaters which control CD moisture variations, thermal actuators which affect sheet thickness, and other known devices. CD actuators present an extensive control problem since sheet-forming machines can easily have several hundred CD actuators spread across the entire machine width to reduce sheet variability.

Adjustment of CD actuators generally affects a portion of the profile which is wider than the area occupied by the individual actuator. Thus, for controlling the CD profile of a web forming machine, it is important to know which portion of the profile is affected by each CD actuator. The functional relationship that describes which part of the profile is affected by each CD actuator is called "mapping" of the CD actuators. The functional curve that indicates how the process profile is changed by the adjustment of a CD actuator is called the "response shape" of the CD actuators. The mapping and response shape of the CD actuators are referred to herein as the CD responses of the actuators. The machine direction response to CD actuator changes is called the MD dynamics. The combination of the MD dynamics and the CD responses is referred to as the two-dimensional (2D) responses of the CD actuators.

Not only does the CD response of each actuator typically spread over a much wider area than the area occupied by the actuator, but also the CD mapping of an actuator can vary or shift for different operating conditions. To obtain a desired profile for a web of sheet material being formed, it is essential to have two-dimensional (2D) information which closely corresponds to each actuator and also to the different operating conditions which the actuator encounters. Thus, the performance of a CD control application is highly dependent on the accuracy of the models that characterize the responses of all CD actuators. In practice, the actuator response models have to be identified from the sheet-forming machines by performing actuator tests. Using an effective method to identify robust response models is very crucial to achieve the optimal control results for any CD control application.

The profile response as the result of a control action applied to a CD actuator is usually obtained through a so-called "bump" test or a "step" setpoint change to a CD actuator. The responses from adjacent CD actuators usually overlap with one another in the CD direction so that conventional CD bump-tests can only be applied to actuators that are far enough apart to have no overlapping effects in order to separate their responses. This problem is exacerbated where a scanning sensor is used to measure the profile responses. The scanning sensor only measures sheet property profiles along diagonal traces across the sheet width. With the extremely sparse and skew data obtained from a scanning sensor, a bump-test usually takes a long time covering multiple scans of the sensor to establish a reliable response model for any CD actuator across the sheet width. The step bump-test itself also suspends the normal control operation and can cause severe product deviations for long duration tests. To get response models for all actuators, it can take many hours to perform many step bump tests so that it is practically infeasible for any production.

An improvement over conventional bump testing is disclosed in U.S. Pat. No. 5,122,963, which issued to the assignee of the present application and is incorporated herein by reference. In the '963 patent, CD actuator perturbing signals defined by pseudo-random binary sequences are used with multiple signals being selected to be statistically independent of one another so that the responses of multiple CD actuators can be determined at the same time. The perturbing signals are gradually increased in amplitude to a level which can be used for CD analysis yet not perturb the web beyond defined specifications. While the teachings of the '963 patent substantially speed up the determination of CD actuator models over conventional bump tests, they still require a substantial period of time since numerous scans of a scanning sensor are still required to characterize all CD actuators.

Since for many sheet-making processes, the two-dimensional, i.e., machine direction and cross-machine direction, uniformity of sheet properties is a critical quality specification, new methods for getting accurate response models for each CD actuator in a sheet-making process are needed to achieve better sheet uniformity control. Preferably, the testing period and product deviations caused by the tests would be reduced for tuning any CD control application. In addition, the new methods should not only reduce the required testing duration and product deviations, they should also identify the two-dimensional (2D) response of each CD actuator individually.

SUMMARY OF THE INVENTION

This need for modeling the 2D responses of the CD actuators is met by the methods of the present invention wherein a set of random probing sequences, often referred to as probing actions, are applied to a set of CD actuators simultaneously for a period of time which is sufficient for measuring web variations or web measurement changes which result from the probing actions. Both actuator feedback and 2D measurement of sheet property variations are collected during the testing period. The collected data is processed in accordance with the present invention to derive 2D response models for each individual actuator of the set of CD actuators. To minimize product deviations caused by the tests, the probing actions are chosen to be as random as possible and to be of short duration. No prolonged step actions are needed with the novel methods of the present invention. With 2D measurement, the total duration of the test is substantially reduced. The new methods identify global process MD dynamics, CD response shapes and CD locations for each individual CD actuator during a single simultaneous application of the probing actions to the CD actuators.

In accordance with one aspect of the present invention, a method for modeling 2D responses, i.e., MD and CD, of a plurality of CD actuators extending across the width of a machine used for manufacturing a web of sheet material comprises selecting a plurality of random probing sequences corresponding to the plurality of CD actuators and perturbing the plurality of CD actuators with the plurality of random probing sequences. The web of sheet material is measured as it is being formed while perturbing the plurality of CD actuators with the plurality of random probing sequences. The global process MD dynamics of the plurality of CD actuators are estimated. And, a CD response is estimated for each of the plurality of CD actuators by using the plurality of random probing sequences, measurements of the web of sheet material and the estimated global process MD dynamics. The global process MD dynamics and the CD responses form 2D responses for the plurality of CD actuators. To refine the 2D responses, the steps of estimating global process MD dynamics, and estimating a CD response for each of the plurality of CD actuators may be iteratively repeated. The method may further comprise estimating the actuator dynamics of the plurality of CD actuators with the steps of estimating global process MD dynamics of the plurality of CD actuators and estimating a CD response for each of the plurality of CD actuators using the estimated actuator dynamics of the plurality of CD actuators.

The step of estimating global process MD dynamics preferably comprises determining measurement changes in the web of sheet material due to perturbation by the plurality of random probing sequences and calculating eigenvalues-eigenvectors of a covariance matrix of the measurement changes. The eigenvector corresponding to the largest eigenvalue is selected to be a dominant CD profile of the measurement changes. The measurement changes are convoluted with the dominant CD profile of the measurement changes to obtain a temporal evolution of the dominant CD profile in the measurement changes. The estimated changes based on the plurality of random probing sequences and the estimated CD responses of the plurality of CD actuators are convoluted with the dominant CD profile of the measurement changes to obtain a temporal evolution of the dominant CD profile in the estimated changes. The difference between the temporal evolution of the dominant CD profile in the measurement changes and the temporal evolution of the dominant CD profile in the estimated changes processed by a selected global process MD dynamics is taken to form a MD modeling error. The MD modeling error is minimized by selecting an optimal global process MD dynamics model, and the optimal global process MD dynamics model is used as an estimated global process MD dynamics.

Preferably, the step of calculating eigenvalues-eigenvectors of the measurement changes comprises decomposing the covariance matrix of the measurement changes using singular value decomposition. And the step of selecting the eigenvector corresponding to the largest eigenvalue to be a dominant CD profile of the measurement changes comprises selecting a dominant CD profile of the measurement changes from a factor obtained from the singular value decomposition of the covariance matrix of the measurement changes.

The step of estimating a CD response for each of the plurality of CD actuators may comprise predicting measurement changes in the web of sheet material due to perturbation by the plurality of random probing sequences using the estimated global process MD dynamics and a selected CD response for each of the plurality of CD actuators. The difference between the measurement changes and predicted measurement changes is then taken to form a CD modeling error. The Frobenius norm of the CD modeling error is minimized by selecting an optimal CD response for each of the plurality of CD actuators. The optimal CD responses for the plurality of CD actuators which minimize the Frobenius norm of the CD modeling error are used as the estimated CD responses for the plurality of CD actuators. The optimal CD responses for the plurality of CD actuators which minimize the Frobenius norm of the CD modeling errors is expressed by the equation $$\hat{G} = [\Delta Y] \tilde{W}^T [\tilde{W} \tilde{W}^T]^{-1}.$$

The method may further comprise repeating the steps of: determining estimated changes in measured sheet material based on the plurality of random probing sequences and the estimated CD responses of the plurality of CD actuators; convoluting the estimated changes with the dominant CD profile of the measurement changes to obtain a temporal evolution of the dominant CD profile in the estimated changes; taking the difference between the temporal evolution of the dominant CD profile in the measurement changes and the temporal evolution of the dominant CD profile in the estimated changes processed by a selected global process MD dynamics to form a MD modeling error; minimizing the MD modeling error by selecting an optimal global process MD dynamics model; using the optimal global process MD dynamics model resulting from minimizing the MD modeling error as an estimated global process MD dynamics predicting measurement changes in the web of sheet material due to perturbation by the plurality of random probing sequences using the estimated global process MD dynamics and a selected CD response for each of the plurality of CD actuators; taking the difference between the measurement changes and predicted measurement changes to form a CD modeling error; minimizing the Frobenius norm of the CD modeling error by selecting an optimal CD response for each of the plurality of CD actuators; and, using the optimal CD responses for the plurality of CD actuators which minimize the Frobenius norm of the CD modeling error as the estimated CD responses for the plurality of CD actuators.

The method may further comprise removing variations that are not associated with actuator responses from the estimated CD responses for the plurality of CD actuators, for example, by smoothing the estimated CD responses for the CD actuators. The estimated CD responses may be further refined by selecting one of the CD responses as an initial reference response. All remaining CD responses are shifted in the cross direction into alignment with the initial reference response to determine relative CD response locations and to define a group of overlapping CD responses. A mean response is determined from the group of overlapping CD responses. The CD responses are shifted in the cross machine direction into alignment with the mean response to determine new relative CD response locations and define a new group of overlapping CD responses. A new mean response is determined from the new group of overlapping CD responses. The steps of shifting said CD responses in the cross machine direction into alignment with said mean response and determining a new mean response are repeated until the new mean response converges within a selected tolerance to form a converged new mean response which is then used as the mean response. Variation bounds are set above and below the mean response. A family of probable CD responses are generated within the variation bounds. An optimal gain is selected and a most probable response is selected from the family of probable responses for each CD actuator response. The CD response for each CD actuator is replaced with the most probable response multiplied by the selected optimal gain and shifted by an appropriate amount for each CD actuator.

The method may further comprise determining CD response boundaries of all CD responses beyond which boundaries the magnitudes of the mean response consistently become smaller than a specified percentage of a maximum of the mean response, and the CD responses outside the boundaries are replaced with zero. Preferably, the variation bounds are set according to a specified confidence level, for example, according to a multiple of a standard deviation of all CD responses. The step of generating a family of probable CD responses within the variation bounds may comprise stretching or compressing the mean response with spline-interpolation.

In accordance with another aspect of the present invention, a method for refining a plurality of CD responses for a corresponding plurality of CD actuators extending across the width of a machine used for manufacturing a web of sheet material comprises selecting one of the CD responses as a reference response. All remaining CD responses are shifted in the cross direction into alignment with the initial reference response to determine relative CD response locations and to define a group of overlapping CD responses. A mean response is determined from the group of overlapping CD responses. The CD responses are shifted in the cross machine direction into alignment with the mean response to determine new relative CD response locations and define a new group of overlapping CD responses. A new mean response is determined from the new group of overlapping CD responses. The steps of shifting said CD responses in the cross machine direction into alignment with said mean response and determining a new mean response are repeated until the new mean response converges within a selected tolerance to form a converged new mean response which is thereafter used as the mean response. Variation bounds are set above and below the mean response. A family of probable CD responses are generated within the variation bounds. An optimal gain is selected and a most probable response is selected from the family of probable responses for each CD actuator response. The CD response for each CD actuator is replaced with the most probable response multiplied by the selected optimal gain and shifted by an appropriate amount for each CD actuator.

The method may further comprise determining CD response boundaries of all CD responses beyond which boundaries the magnitudes of the mean response consistently become smaller than a specified percentage of a maximum of the mean response, and the CD responses outside the boundaries are replaced with zero. Preferably, the variation bounds are set according to a specified confidence level, for example, according to a multiple of a standard deviation of all CD responses. The step of generating a family of probable CD responses within the variation bounds may comprise stretching or compressing the mean response with spline-interpolation.

It is, thus, an object of the present invention to provide improved methods for getting accurate 2D response models for each CD actuator in a sheet-making process to achieve better sheet uniformity control.

Other objects and advantages of the invention will be apparent from the following description, the accompanying drawings and the appended claims.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIG. 1 is two-dimensional view of a probing or perturbation matrix made up by a plurality of random probing sequences;

FIG. 1A is a graphical representation of a sequence of random probing actions which comprise a row of the probing or perturbation matrix of FIG. 1;

FIG. 1B is a graphical representation of the five random probing actions of the probing or perturbation matrix of FIG. 1;

FIG. 2 is an illustration of two-dimensional measurement changes in a web of sheet material being formed by a web manufacturing machine while a plurality of cross-machine direction actuators extending across the width of the machine are probed or perturbed by the plurality of random probing sequences making up the perturbation matrix of FIG. 1;

FIG. 3 is a graph of a dominant CD profile of measurement changes resulting from the perturbation of the plurality of CD actuators of the web forming machine;

DETAILED DESCRIPTION OF THE INVENTION

Figure 4:
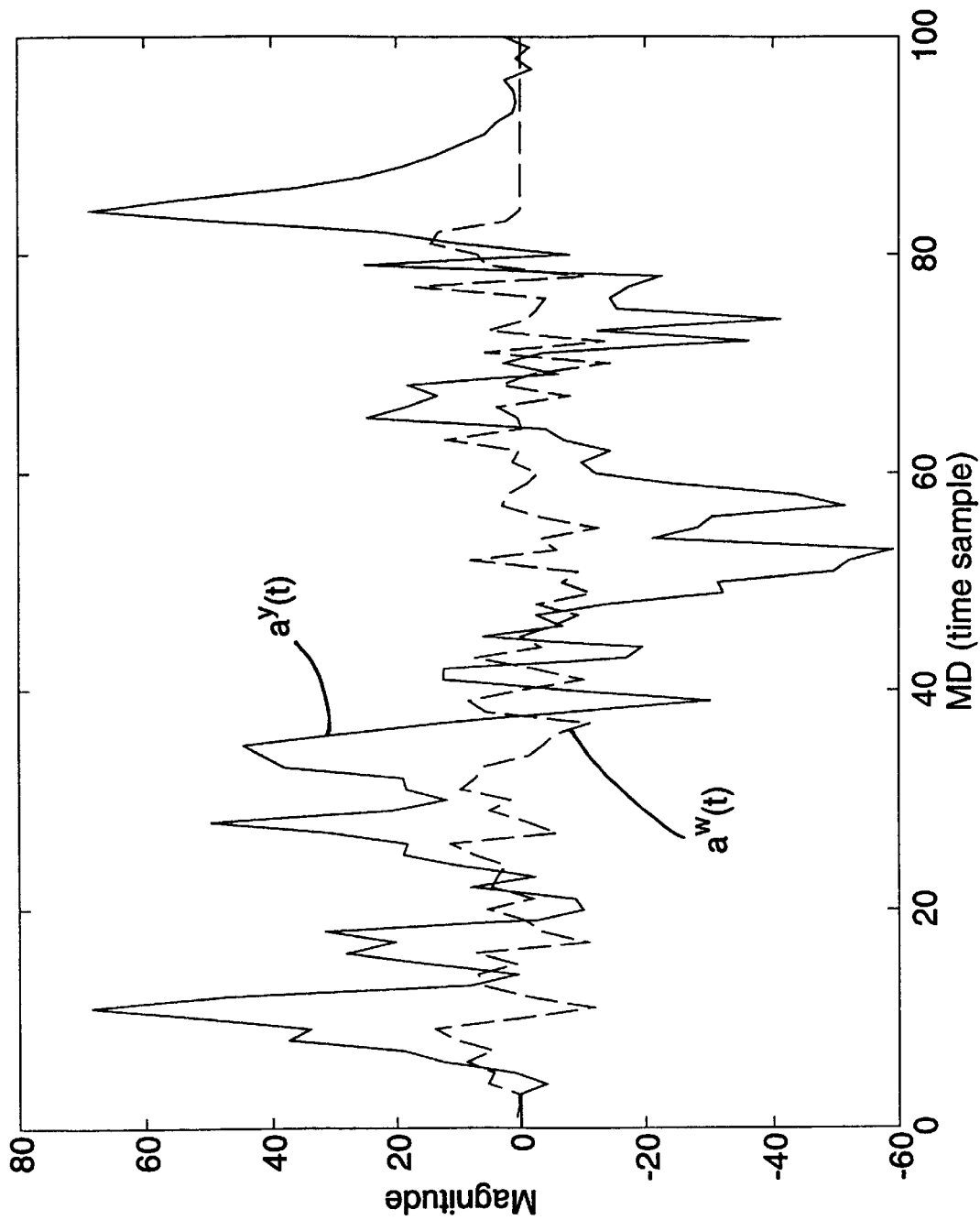
FIG. 4 is a graph illustrating the temporal evolution of the dominant CD profile of FIG. 3 in the measurement changes $a^y(t)$ and the temporal evolution of the dominant CD profile of FIG. 3 in the estimated changes $a^w(t)$.

The invention of the present application will now be described with reference to the drawings wherein FIG. 1 shows a probing or perturbation matrix W made up by a plurality of random probing sequences as illustrated in FIG. 1. A first example 102 of one random probing sequence is illustrated in FIG. 1A and five random probing sequences 104–112 are illustrated in FIG. 1B. In the probing matrix W of FIG. 1, there are n rows and s columns where n=45 and s=100. Each row of the perturbation matrix of FIG. 1 comprises a sequence of random probing actions, see FIGS. 1A and 1B, which is applied to a corresponding one of a like plurality of CD actuators of a machine used for manufacturing a web of sheet material, for example, a paper making machine for which the present invention is particularly applicable and initially being applied as illustrated, for example, in referenced U.S. Pat. No. 5,122,963.

The magnitude and duration of each probing action can be randomly selected. However, the minimal duration of each action in the sequence is selected such that the response of each action is observable in two-dimensional (2D) measurement data; and, the maximum magnitude of each action is selected within a maximum range of magnitudes 114, 116, see FIG. 1A, such that the application of the probing actions to the CD actuators of the web manufacturing machine does not make the web exceed specifications for the web of material. Accordingly, the web of material produced during application of the probing actions should be within required web specifications and therefore usable in spite of the perturbations.

The 2D measurement data is preferably obtained using non-scanning, full-sheet measurement which has recently become commercially available to measure the entire sheet width without movement of sensors back and forth across the sheet and without missing any portions of the sheet, see U.S. Pat. No. 5,563,809 which is incorporated herein by reference. Such measurements can be taken at almost any location along a web-forming process. Using these 2D measuring techniques, a massive amount of full-width, truly two-dimensional measurement data is available almost continuously. Using such 2D measurement techniques, the duration of the probing actions typically ranges from a few seconds to a minute whereas with conventional scanning measurements, step bump tests usually have to last for multiple scans, i.e., several minutes to a half-hour, in order to get the full measurement of actuator responses.

To enable all CD actuators to be probed or perturbed at the same time, the probing sequences for the CD actuators should not be identical to one another and no probing sequence should be equal to a linear combination of two or more probing sequences used for other CD actuators. Under these conditions, the number of probing actions in the probing sequences has to be at least equal to or greater than the number of probing actuators. To reduce the number of probing sequences required for probing all CD actuators, the CD actuators can be divided into a number of groups, three groups 118, 120, 122 are illustrated in FIG. 1. The number of CD actuators in each group is selected so that the responses from the two edge actuators in each group, i.e., the CD actuators at the two ends or edges of the group, do not overlap and hence have no effect on a common portion of the web. For such grouping of the actuators, a smaller set of probing sequences which are shorter in length can be used for all of the groups of CD actuators. For the grouping arrangement, the length of the probing sequences is substantially reduced so that typically the total probing time duration required will only be a few minutes depending on the number of CD actuators in each of the groups.

In practice, the duration of each probing action is set to be an integer multiple of a base sampling period. In a working embodiment of the present invention used for slice lip control in a paper making machine, the base sampling time was 1 to 3 seconds. The probing sequences for a group of actuators form a two-dimensional matrix. For the following analysis, the 2D random probing actions are represented by rows of an nxs matrix W or W(t):

$$W = W(t) = \begin{bmatrix} w_1 \\ w_2 \\ \vdots \\ w_i \\ \vdots \\ w_n \end{bmatrix}_{nxs}$$

where n is the number of CD actuators and hence probing sequences in the group. The probing sequence $w_i$ for the i-th CD actuator is a row vector with s sampling periods. While statistically uncorrelated probing sequences are preferred for the present invention, it is not necessary to have each probing sequence perfectly uncorrelated with the other probing sequences. The present invention will work with almost any random sequences used as probing sequences as described above.

Initially, approximate 2D responses of the CD actuators can be determined by probing only one CD actuator near the center of the web of sheet material or several actuators spread across the full width of the web and separated from one another with a very short duration test. The response or responses from this probing test would then be used to determine an initial approximation of the global process MD dynamics, $\hat{g}_0$, as used in the following processing and shown in FIG. 11. If the probing test is not performed, $\hat{g}_0$ can simply be set equal to 1 as a starting value. As should be apparent from this description, it is also possible in the present invention to start with an estimate of the CD responses $\hat{G}$ in the following processing, see FIG. 11 and equation (5), if the probing test is performed. However, if no probing test is performed, then the processing as described hereinafter and shown in FIG. 11 staring with $\hat{g}_0$ should be followed. In view of the simplicity and flexibility, starting with $\hat{g}_0$ is currently preferred.

The probing sequences $w_i$ of the probing or perturbation matrix W of FIG. 1 are applied to CD actuators of a web forming machine, for example slice lip actuators of a paper making machine, for a total duration of s sampling periods, s=100 in FIG. 1. The impacts of the probing actions are observed from a non-scanning full-sheet sensor, for example, a commercial version of the sensor described in referenced U.S. Pat. No. 5,563,809. Both temporal (MD) and spatial (CD) impacts of the probing actions are measured quickly and accurately as a 2D measurement from the non-scanning full-sheet sensor. The measured 2D data is represented by a matrix Y or Y(t):

$$Y = Y(t) = \begin{bmatrix} y_1 \\ y_2 \\ \vdots \\ y_j \\ \vdots \\ y_m \end{bmatrix}_{nxs}$$

where m is the resolution of measurement in the cross-machine direction and $y_j$ is a row vector with s number of samples in the machine direction. For simplicity of formulation, the profile sampling frequency in the machine direction is presumed to be the same as the sampling time of the probing actions. The difference between measured 2D data when the probing actions are applied to the CD actuators and measured 2D data when the probing actions are zero or not applied to the CD actuators is defined by the measurement changes, $\Delta Y=Y(t)-Y_0$, illustrated in FIG. 2.

For example, the probing actions of the perturbation matrix W shown in FIG. 1 were applied to CD actuators of a machine, slice lip controllers of a paper making machine, which had 45 CD actuators. FIG. 2 shows the measurement changes, $\Delta Y=Y(t)-Y_0$, obtained from a non-scanning sensor, such as a commercial version of the sensor described in referenced U.S. Pat. No. 5,563,809, while the probing actions were applied to the CD actuators.

The 2D measurement Y(t) is related to the probing action W(t) through the 2D responses by the equation:

$$Y(t)=Gg(q^{-1})H(q^{-1})W(t)+Z(t)+Y_0 \qquad (1)$$

In equation (1), G is an mxn matrix representing the spatial direction (CD) response models for the n CD actuators. $H(q^{-1})$ is an nxn diagonal matrix with its diagonal terms representing the actuator dynamics for the n CD actuators. The term $g(q^{-1})$ is the global process MD dynamics. The symbol $q^{-1}$ represents discrete time shifting in the machine direction. $H(q^{-1})$ and $g(q^{-1})$ are discretized dynamics models of the corresponding continuous actuator dynamics and process dynamics. Z(t) is an mxs matrix representing the random noise in the process and/or the measurement. $Y_0$ is an mxs matrix that represents the stationary 2D web data which is measured when the machine is operated without the probing sequences applied to the CD actuators, i.e., measurement data of the normal web manufactured by the machine without the probing perturbations.

Figure 11:
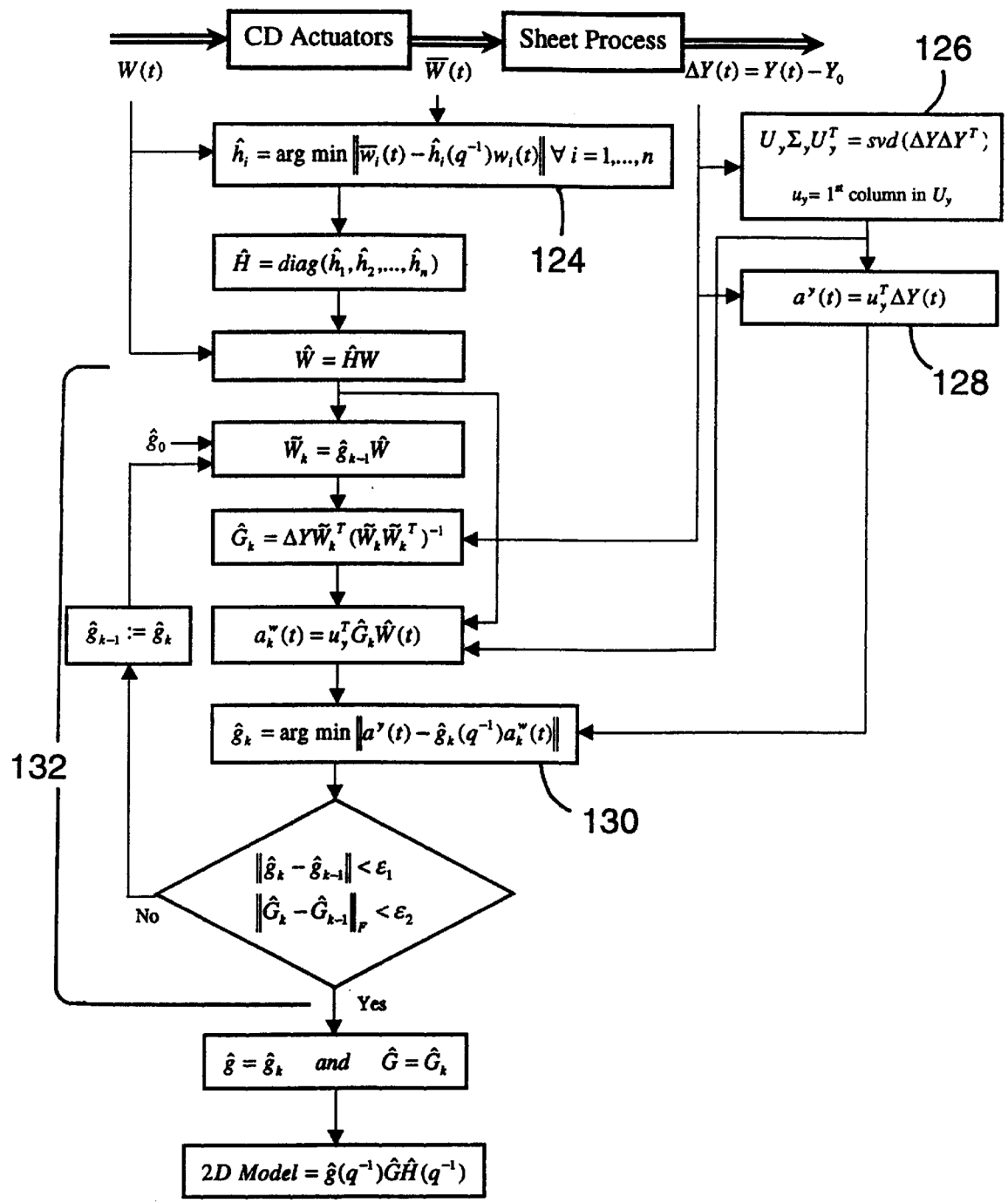
FIG. 11 is a flow chart of the operations leading to the estimated MD dynamics and estimated CD response models or CD responses for the plurality of CD actuators as these estimated 2D responses are illustrated in FIGS. 5 and 6.

The actuator dynamics of the CD actuators, see 124 in FIG. 11, i.e., the diagonal terms in the matrix $H(q^{-1})$, can be determined individually from the probing sequence applied to each CD actuator and the action feedback, such as actuator position feedback, from the corresponding actuator, see FIG. 11. Any standard identification scheme can be used to determine the MD dynamics of the CD actuators. Assuming that the actuator dynamics are of the first order with dead-time delay, a searching method such as the Nelder-Mead method can be used to minimize the difference between the predicted actuator output and the actual actuator feedback for each actuator. While these techniques are well known to those skilled in the art, additional information can be obtained by reference to an article entitled A SIMPLEX METHOD FOR FUNCTION MINIMIZATION by J. A. Nelder and R. Mead which was published in Computer Journal, Vol. 7 pages 308–313 (1965) and is incorporated herein by reference. Optimal actuator dynamics models for the CD actuators are obtained using the equation:

$$\hat{h}_i(q^{-1})=arg\ min\|\bar{w}_i(t)-\hat{h}_i(q^{-1})w_i(t)\| \forall i=1,\ldots,n \qquad (2)$$

where $\hat{w}_i(t)$ is the action feedback from the i-th actuator and $\hat{h}_i(q^{-1})$ represents the dynamic model of the i-th CD actuator, see 124 of FIG. 11. Typically, $\hat{h}_i(q^{-1})$ has unity gain. Since for most practical applications, actuator dynamics are typically very fast and negligible $\hat{h}_i(q^{-1})$ is equal to one. In our example, the actuator dynamics are assumed to be sufficiently fast so that the diagonal matrix $\hat{H}(q^{-1})$ is approximated with an identity matrix. While these techniques are well known to those skilled in the art, additional information can be obtained by reference to MATLAB OPTIMIZATION TOOLBOX USER'S GUIDE by Mary N. Branch and Andrew Grace which was published by MathWorks, Inc. in 1996 and is incorporated herein by reference.

Figure 5:
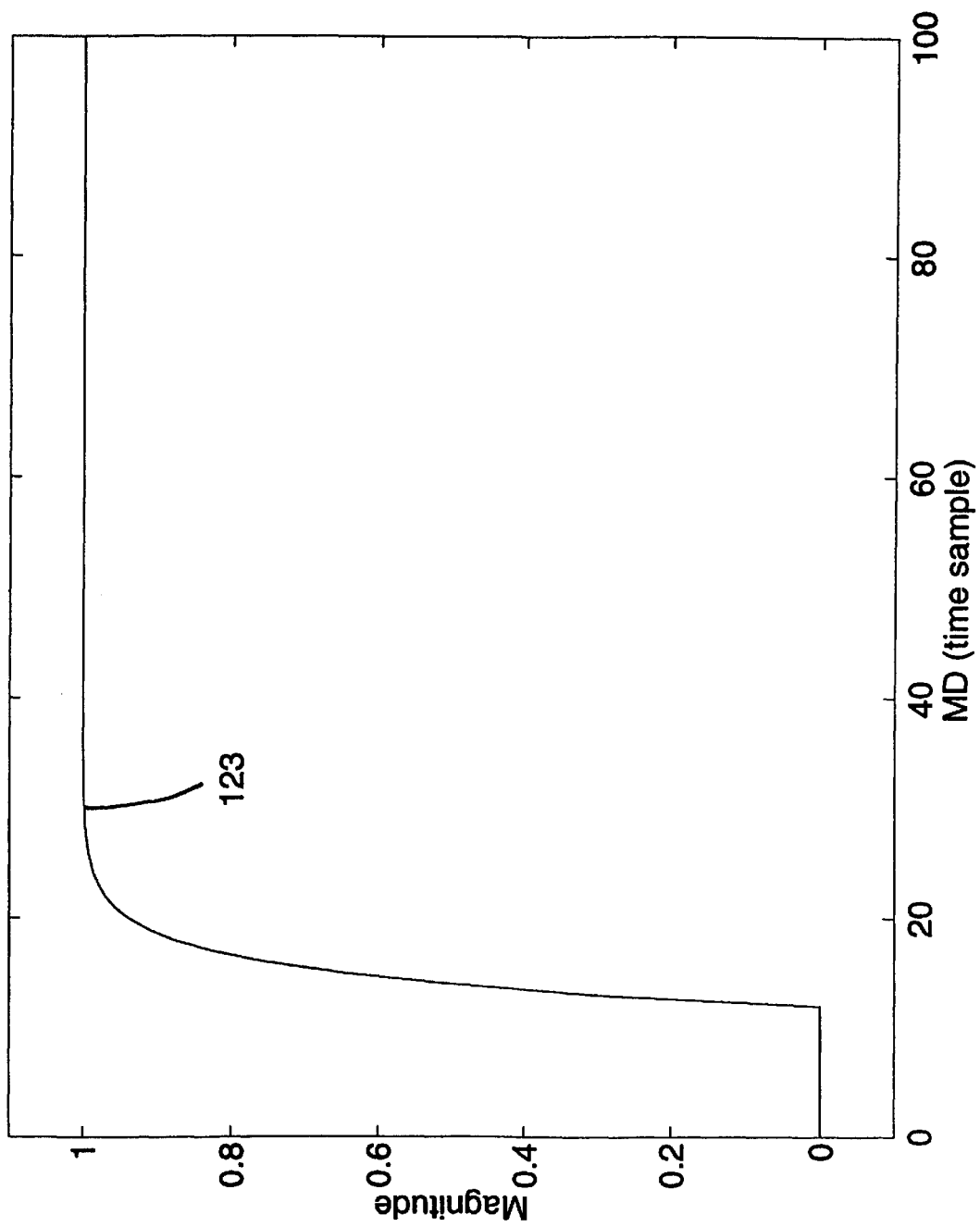
FIG. 5 is a graph of estimated global process MD dynamics for the plurality of CD actuators of the web manufacturing machine.

From observations of the actual process dynamic behavior, applicant has determined that the global MD process dynamics $g(q^{-1})$ 123 is substantially the same for all CD actuators, see FIG. 5. By examining the general characteristics of 2D sheet variations, applicant has also determined that the MD or temporal evolution of a dominant CD profile, $u_y$, in measurement changes, $\Delta Y=Y(t)-Y_0$, is related to the MD evolution of $u_y$ in estimated changes, $GH(q^{-1})W(t)$, through the global MD process dynamics $g(q^{-1})$.

The dominant CD profile $u_y$ of the 2D measurement changes $\Delta Y$ is defined as the eigenvector corresponding to the largest eigenvalue of the covariance matrix of the 2D measurement changes $\Delta Y$, see FIG. 3. This eigenvector can be determined in a number of ways, however, preferably, it is obtained from the singular value decomposition (svd) of the covariance matrix $[\Delta Y][\Delta Y]^T$, see 126 of FIG. 11, which results in the factors $U_y$, $\Sigma_y$ and $V_y$ of the equation:

$$U_y\Sigma_y V_y=svd([\Delta Y][\Delta Y]^T) \qquad (3)$$

The diagonal matrix factor $\Sigma_y$ contains singular values in the descending order. The first column $u_y$ in the matrix factor $U_y$ is the dominant CD profile of the 2D measurement changes $\Delta Y$, see FIG. 3. While these techniques are well known to those skilled in the art, additional information can be obtained by reference to, for example, the fourth edition of LINEAR ALGEBRA WITH APPLICATIONS by Steven J. Leon published by the Macmillan College Publishing Company which is incorporated herein by reference.

As shown in FIG. 4, the temporal evolution $a^y(t)$ of $u_y$ in the measurement changes $\Delta Y$ is obtained by convolution, see 128 of FIG. 11, from the equation:

$$a^y(t)=u_y^T[\Delta Y] \qquad (4)$$

And, the temporal evolution $a^w(t)$ of $u_y$ in the estimated changes $GH(q^{-1})W(t)$ is obtained from the equation:

$$a^w(t)=u_y^T[GH(q^{-1})W(t)] \qquad (5)$$

For the first calculation of $a^w_{(t)}$ in equation (5), G can be either approximated with any pre-knowledge about the actuator CD response, for example the response or responses obtained from the probing test previously mentioned, or simply ignored. In the subsequent iterative calculations, the CD response G and $g(q^{-1})$ will be available from the recursive calculation of the following operations. The dynamic relationship between $a^y(t)$ and $a^w(t)$ is the global MD process dynamics $g(q^{-1})$. The global MD process dynamics model $\hat{g}(q^{-1})$ is obtained by minimizing the modeling error $a^y(t)-\hat{g}(q^{-1})\ a^w(t)$ using equation (6), see 130 of FIG. 11:

$$\hat{g}(q^{-1})=arg\ min\|a^y(t)-\hat{g}(q^{-1})a^w(t)\| \qquad (6)$$

The optimization can be performed with searching methods such as the Nelder-Mead optimization method. See the referenced article by J. A. Nelder and R. Mead. The resulting model $\hat{g}(q^{-1})$ is normalized to a unity gain for the subsequent calculations.

With $\hat{H}(q^{-1})$ and $\hat{g}(q^{-1})$ identified from the preceding operations, the probing actions that have included the MD process dynamics are calculated to determine an intermediate probing action matrix $\tilde{W}(t)$ using the equation:

$$\tilde{W}(t)=\hat{g}(q^{-1})\hat{H}(q^{-1})W(t) \qquad (7)$$

The 2D sheet variation is predicted or estimated with the 2D model using the following equation for the predicted 2D sheet variation $\hat{Y}$:

$$\hat{Y}(t) = \hat{G}\hat{g}(q^{-1})\hat{H}(q^{-1})W(t) + Y_0 = \hat{G}\tilde{W}(t) + Y_0 \quad (8)$$

The optimal CD response $\hat{G}$ is identified as the model that minimizes the Frobenius norm of the difference between the 2D measurement changes $\Delta Y = Y - Y_0$ and the estimated 2D sheet variation $\Delta\hat{Y} = \hat{Y} - Y_0$, i.e., $\|Y - \hat{Y}\|_F^2$.

The optimal solution of the estimated CD response $\hat{G}$ is then determined using the equation:

$$\hat{G} = [Y - Y_0]\tilde{W}^T[\tilde{W}\tilde{W}^T]^{-1} \quad (9)$$

Figure 6:
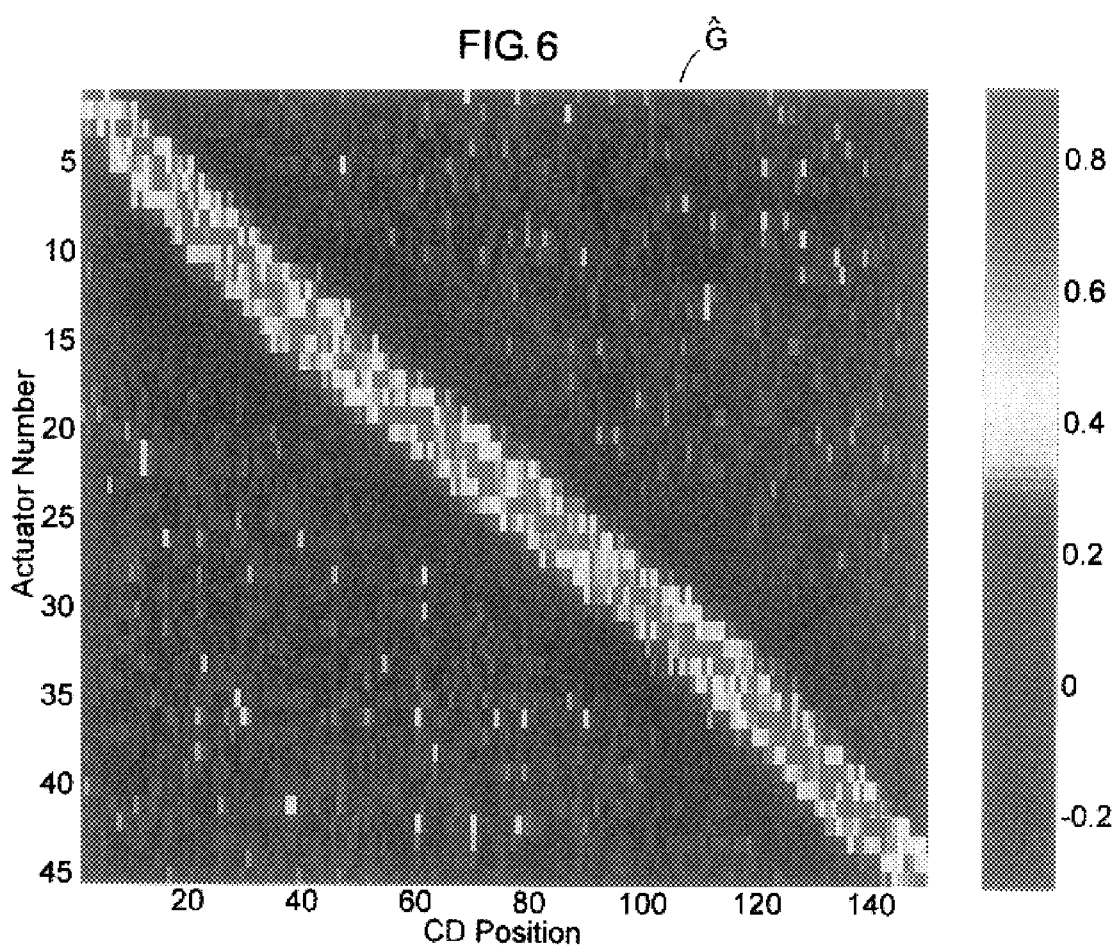
FIG. 6 is a two-dimensional representation of estimated CD response models or CD responses for the plurality of CD actuators of the web manufacturing machine determined in accordance with the present invention.

FIG. 6 shows the CD response model $\hat{G}$ identified from the probing actions of FIG. 1 and the 2D measurement changes of FIG. 2 using the equation (9). Solving equations (5)–(9) can be iterated to refine both MD and CD response models until both MD and CD models converge. The iteration process is illustrated by reduced or simplified equations in the portion of the flow chart of FIG. 11 designated by the identifying numeral 132.

Variations that are not associated with CD actuator responses are removed from the estimated CD responses for the plurality of CD actuators by smoothing the CD actuator responses. Smoothing may be performed by filtering, for example as disclosed in referenced U.S. Pat. No. 5,122,963, wavelet decomposition or other appropriate techniques. It is believed that wavelet decomposition is well known to those skilled in the art; however, for additional information readers are referred to an article entitled *Wavelet analysis* by Bruce et al. in the October 1996 issue of IEEE Spectrum magazine and a book entitled *Wavelets and Filter Banks* by Gilbert Strang and Truong Nguyen published by Wellesley Cambridge Press in 1996 (ISBN 0961408871) which are incorporated by reference herein. After the CD response profiles in $\hat{G}$ have been processed to remove such variations, one complete CD response profile in $\hat{G}$ is taken to be an initial reference profile $g_r(x)$. Typically the initial reference profile $g_r(x)$ is taken near the center or midpoint of the web of material being manufactured and, in any event, the initial reference profile $g_r(x)$ is taken away from the edges of the web. All other CD responses are then shifted toward the initial reference profile or response to determine the relative CD response locations, a mean response profile 134 and to define a group of overlapping CD responses 136, see FIG. 7. The relative CD response location $c_i$ of the i-th actuator is determined by minimizing the following norm:

$$J_i = \|\hat{g}_i(x - c_i) - g_r(x)\|^2 \quad (10)$$

In equation (10), x represents the CD coordinate, $g_r(x)$ is the reference response profile, $\hat{g}_i(x)$ is the i-th response profile (column) in model $\hat{G}$, and $c_i$ is the CD shifting applied to $\hat{g}_i(x)$.

Applying the above shifting for all response profiles in $\hat{G}$, the total norm $J_r$ as defined in the following equation is minimized.

$$J_r = \sum_{i=1}^{n} \|\hat{g}_i(x - c_i) - g_r(x)\|^2 \quad (11)$$

After all $c_i$ are determined from minimizing $J_r$, the mean response profile $g_m(x)$ is calculated as the average of all $\hat{g}_i(x - c_i)$. The mean response profile $g_m(x)$ minimizes $J_m$ as defined in the following equation:

$$J_m = \sum_{i=1}^{n} \|\hat{g}_i(x - c_i) - g_m(x)\|^2 \quad (12)$$

The calculation of shifting parameter $c = [c_1 \ c_2 \ c_3 \ \ldots \ c_n]$ and $g_m(x)$ can be recursively iterated by minimizing $J_r$ and $J_m$ in equations (11) and (12) by repeatedly replacing $g_r(x)$ in equation (11) with $g_m(x)$ as calculated in equation (12) until $g_m(x)$ converges within a selected tolerance, for example to less than 1% of the standard deviation of the mean profile response.

Figure 7:
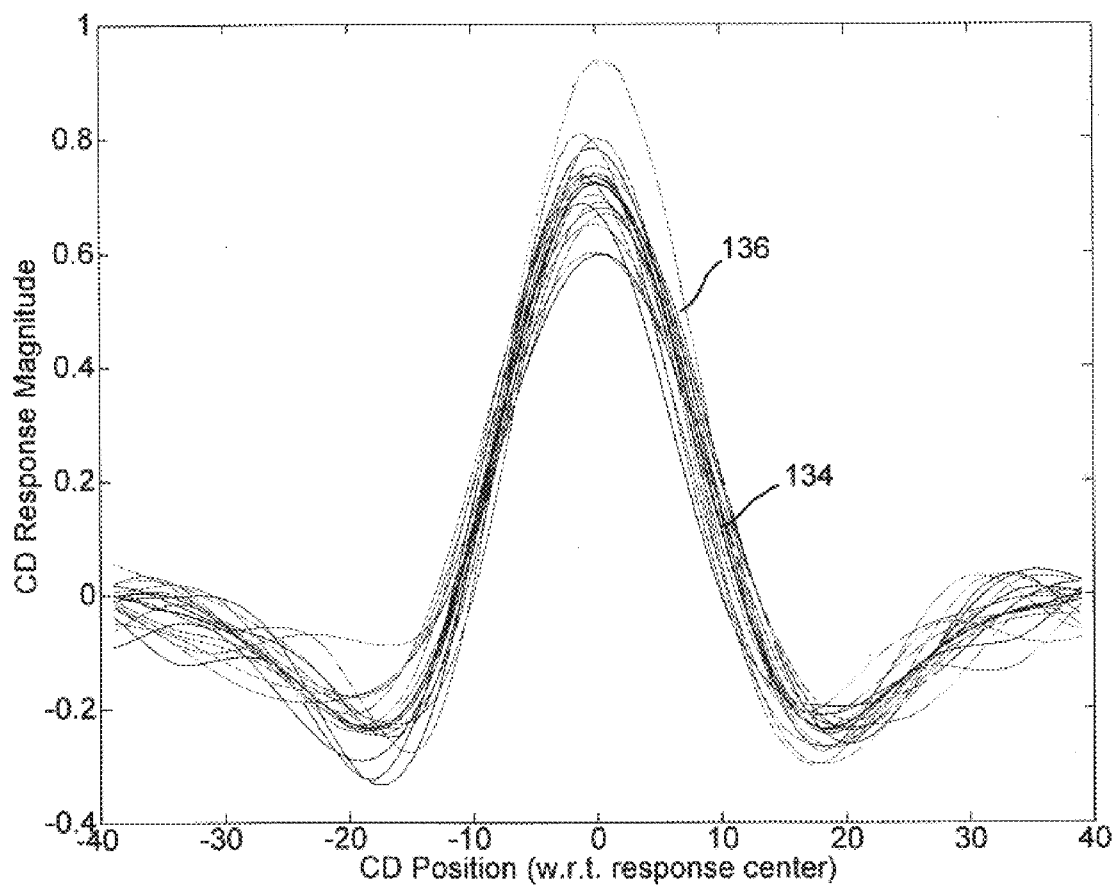
FIG. 7 illustrates selection of a reference CD response and a shifting of all remaining CD responses into alignment with the reference CD response to define a group of overlapping CD responses.
Figure 8:
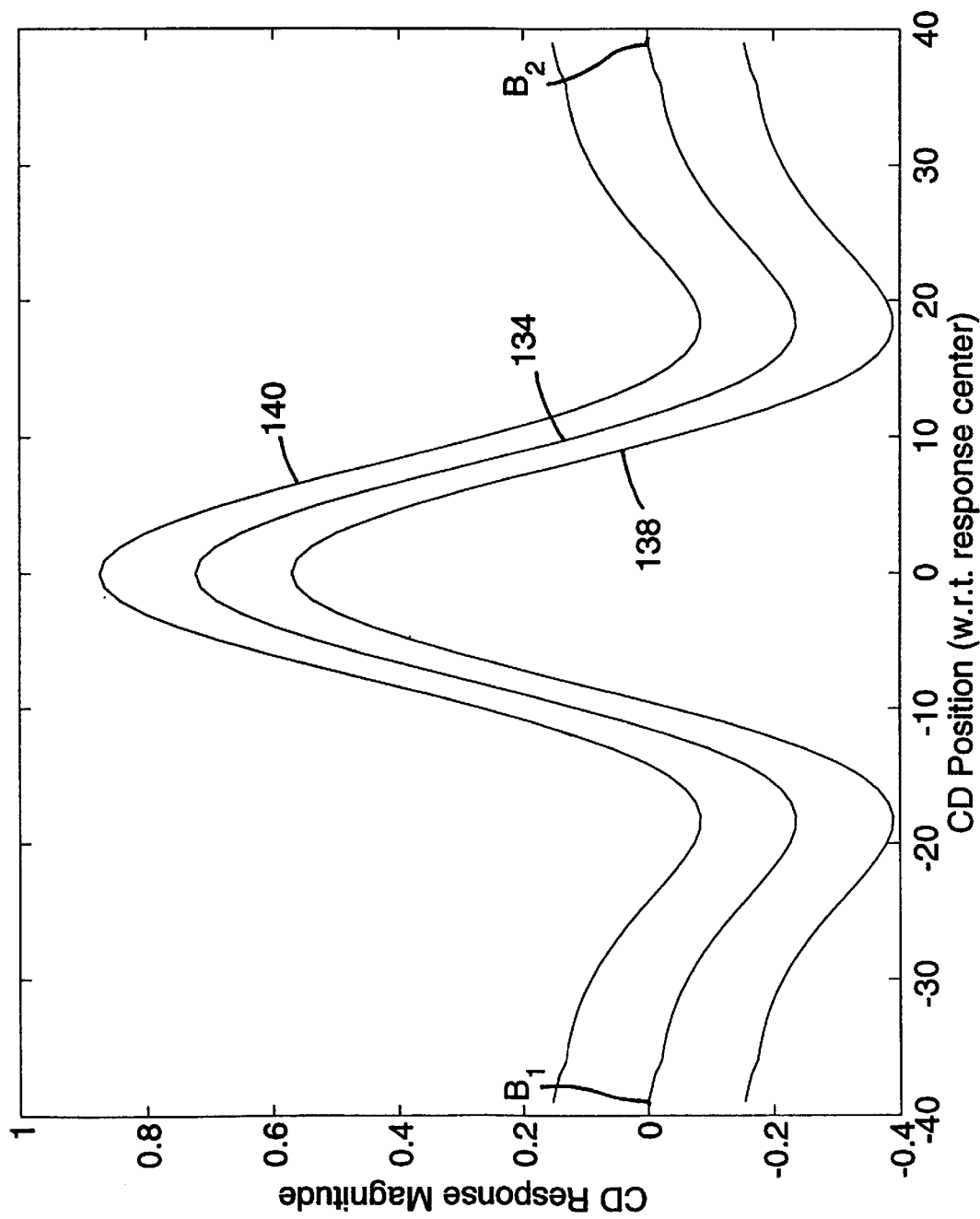
FIG. 8 illustrates a mean response determined from the group of overlapping CD responses of FIG. 7 and variation bounds set above and below the mean response.

CD response boundaries $B_1$, $B_2$ of all CD response shapes are determined from the mean response profile 134, $g_m(x)$, by taking a specified percentage, for example 1% to 5%, of the maximum magnitude of the mean response profile 134 and comparing the magnitudes of the mean response to the specified percentage of its maximum magnitude. The response boundaries B1, B2 are define by points beyond which the magnitudes of the mean response are consistently smaller than the specified percentage of its maximum response. The CD responses beyond the CD response boundaries $B_1$, $B_2$ are negligible and are replaced by zero. With the mean response profile and all shifted responses, variation bounds of the response shape are calculated according to a specified statistical confidence level. FIG. 8 shows the mean response profile 134 and the 3-times standard deviation bounds 138, 140 for all CD responses that are shown in FIG. 7.

Figure 9:
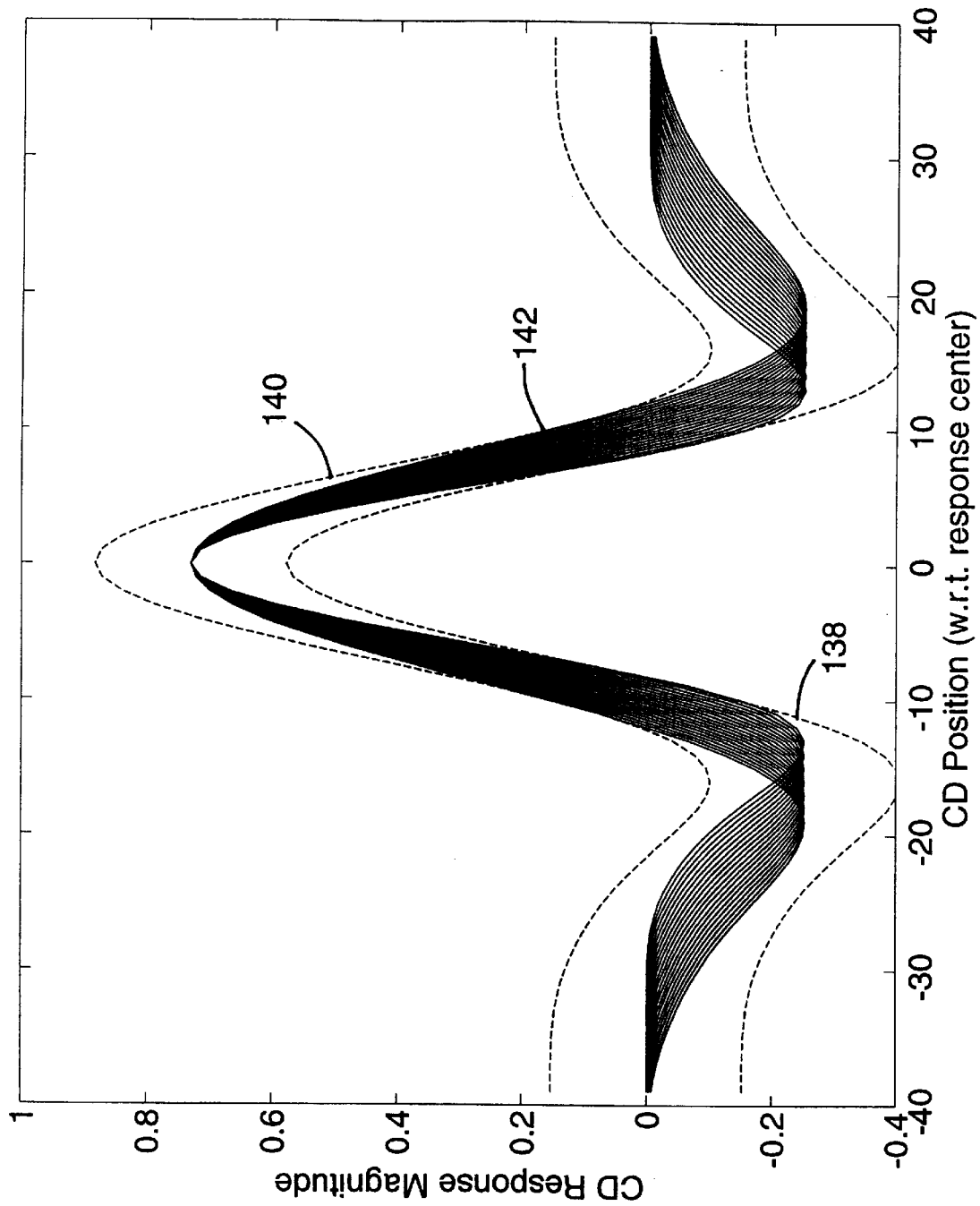
FIG. 9 illustrates a family of probable CD responses generated within the variation bounds of FIG. 8.

Within the variation bounds, for example the 3-times standard deviation bounds 138, 140, the mean response profile $g_m(x)$ can be stretched or compressed using spline-interpolation to generate a family of probable response profiles 142 called $p_k(x)$ as shown in FIG. 9. While these techniques are well known to those skilled in the art, additional information can be obtained by reference to A PRACTICAL GUIDE TO SPLINES by C. deBoor which was published by Springer Verlog (1978) and is incorporated herein by reference.

For each actuator response $\hat{g}_i(x)$ in $\hat{G}$, a most probable response profile from the family of $p_k(x)$ is selected to minimize the error norm $J_i^p$ defined by the equation:

$$J_i^p = \|\hat{g}_i(x) - b p_k(x)\| \quad (13)$$

where b is a gain factor and $p_k(x)$ is selected from the probable response profiles within the confidence bounds.

Figure 10:
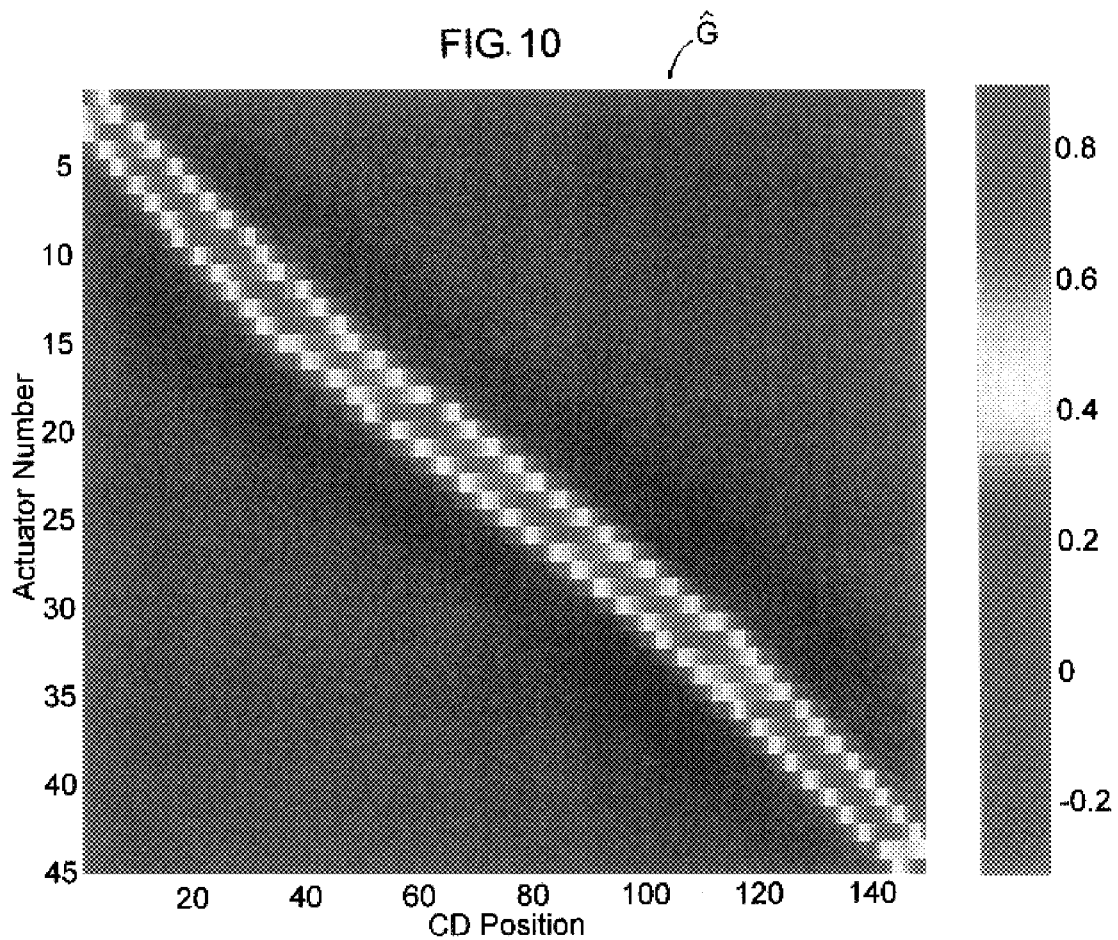
FIG. 10 is a two-dimensional representation of most probable CD response models or CD responses for the plurality of CD actuators of the web manufacturing machine determined in accordanc present invention.

The optimal gain b* and the probable profile p*(x) that minimizes the error norm $J_i^p$ is considered to be the most probable response for the i-th actuator, hence $\hat{g}_i(x)$ is replaced by the most probable response profile $b^*p^*(x)$ with the proper CD shifting $c_i$. This optimization is carried out for each CD actuator. The final modified response model is what can be used in a CD control application. FIG. 10 shows the final CD response model $\hat{G}$ as the result of the present invention. The final CD response model $\hat{G}$ together with $\hat{H}(q^{-1})$ and $\hat{g}(q^{-1})$ determined in as described above form the complete 2D response model for all CD actuators in the machine.

The identification methods of the present invention as described above have a number of key advantages:

1. The invention determines full 2D response models for any subset of CD actuators or all CD actuators simultaneously by probing all of CD actuators at the same time with a very short perturbing time period. The response model and location of each individual actuator are obtained simultaneously.

2. The two-dimensional response of each actuator is modeled individually. The precise location of each response profile is determined from the probing test directly, not estimated from its adjacent actuator responses. The localized nonlinear shrinkage can be easily identified and directly appear in the model. Such detailed shrinkage or mapping behavior is very crucial to control modern CD actuators such as headbox dilution valves in paper machines.

3. The superposition of the responses of random probing actions reduces the risk of producing off-specification products while the methods of the present invention are being applied. The conventional bumptest makes step changes to actuators far apart to ensure that no responses are overlapping with each other. The major drawback of the conventional bump-test is that it can cause severe off-specification product deviations for an entire testing period.

4. The short duration of the described methods reduces testing time and minimizes the impact of the testing on production. The methods of the present application fully utilize the advantages of non-scanning measurement techniques. The two-dimensional fast-sampled data allows the impacts of random actions to be quickly detected and the duration of each probing action is significantly reduced again reducing the production impact of the methods of the present application.

5. Since the methods of the present application have a substantially reduced impact on web products being produced, testing can be performed more frequently which improves the control of the machine. That is, the CD models conform more accurately to the actual process behavior so that better CD control performance can be achieved by the machine control systems.

Having thus described the invention of the present application in detail and by reference to preferred embodiments thereof, it will be apparent that modifications and variations are possible without departing from the scope of the invention defined in the appended claims.

What is claimed is:

1. A method for modeling two-dimensional (2D) responses, machine direction (MD) and cross-machine direction (CD), of a plurality of CD actuators extending across the width of a machine used for manufacturing a web of sheet material, said method comprising the steps of:

selecting a plurality of random probing sequences corresponding to said plurality of CD actuators;

perturbing said plurality of CD actuators with said plurality of random probing sequences;

measuring said web of sheet material being formed while perturbing said plurality of CD actuators with said plurality of random probing sequences;

estimating global process MD dynamics of said plurality of CD actuators; and estimating a CD response for each of said plurality of CD actuators by using said plurality of random probing sequences, measurements of said web of sheet material and estimated global process MD dynamics, said global process MD dynamics and said CD responses forming 2D responses for said plurality of CD actuators.

2. A method as claimed in claim 1 further comprising repeating the steps of estimating global process MD dynamics, and estimating a CD response for each of said plurality of CD actuators to thereby refine said 2D responses for said plurality of CD actuators.

3. A method as claimed in claim 1 further comprising the step of estimating the actuator dynamics of said plurality of CD actuators, said steps of estimating global process MD dynamics of said plurality of CD actuators and estimating a CD response for each of said plurality of CD actuators using estimated actuator dynamics of said plurality of CD actuators.

4. A method as claimed in claim 1 wherein said step of estimating global process MD dynamics comprises the steps of:

determining measurement changes in said web of sheet material due to perturbation by said plurality of random probing sequences;

calculating eigenvalues-eigenvectors of a covariance matrix of said measurement changes;

selecting the eigenvector corresponding to the largest eigenvalue to be a dominant CD profile of said measurement changes;

convoluting said measurement changes with said dominant CD profile of said measurement changes to obtain a temporal evolution of said dominant CD profile in said measurement changes;

determining estimated changes in measured sheet material based on said plurality of random probing sequences and said estimated CD responses of said plurality of CD actuators;

convoluting said estimated changes with said dominant CD profile of said measurement changes to obtain a temporal evolution of said dominant CD profile in said estimated changes;

taking the difference between said temporal evolution of said dominant CD profile in said measurement changes and said temporal evolution of said dominant CD profile in said estimated changes processed by a selected global process MD dynamics to form a MD modeling error;

minimizing said MD modeling error by selecting an optimal global process MD dynamics model; and using said optimal global process MD dynamics model resulting from minimizing said MD modeling error as an estimated global process MD dynamics.

5. A method as claimed in claim 4 wherein said step of calculating eigenvalues-eigenvectors of said measurement changes comprises decomposing said covariance matrix of said measurement changes using singular value decomposition, and said step of selecting the eigenvector corresponding to the largest eigenvalue to be a dominant CD profile of said measurement changes comprises the step of selecting a dominant CD profile of said measurement changes from a factor obtained from said singular value decomposition of said covariance matrix of said measurement changes.

6. A method as claimed in claim 4 wherein said step of estimating a CD response for each of said plurality of CD actuators comprises the steps of:

predicting measurement changes in said web of sheet material due to perturbation by said plurality of random probing sequences using said estimated global process MD dynamics and a selected CD response for each of said plurality of CD actuators;

taking the difference between said measurement changes and predicted measurement changes to form a CD modeling error;

minimizing a Frobenius norm of said CD modeling error by selecting an optimal CD response for each of said plurality of CD actuators; and using said optimal CD responses for said plurality of CD actuators which minimize the Frobenius norm of said CD modeling error as the estimated CD responses for said plurality of CD actuators.

7. A method as claimed in claim 6 wherein said optimal CD responses for said plurality of CD actuators which minimize the Frobenius norm of said CD modeling errors is expressed by the equation:

$$\hat{G}=[\Delta Y]\hat{W}^T[\hat{W}\hat{W}^T]^{-1}.$$

8. A method as claimed in claim 6 further comprising the steps of repeating the steps of:
   determining estimated changes in measured sheet material based on said plurality of random probing sequences and said estimated CD responses of said plurality of CD actuators;
   convoluting said estimated changes with said dominant CD profile of said measurement changes to obtain a temporal evolution of said dominant CD profile in said estimated changes;
   taking the difference between said temporal evolution of said dominant CD profile in said measurement changes and said temporal evolution of said dominant CD profile in said estimated changes processed by a selected global process MD dynamics to form a MD modeling error;
   minimizing said MD modeling error by selecting an optimal global process MD dynamics model;
   using said optimal global process MD dynamics model resulting from minimizing said MD modeling error as an estimated global process MD dynamics
   predicting measurement changes in said web of sheet material due to perturbation by said plurality of random probing sequences using said estimated global process MD dynamics and a selected CD response for each of said plurality of CD actuators;
   taking the difference between said measurement changes and predicted measurement changes to form a CD modeling error;
   minimizing the Frobenius norm of said CD modeling error by selecting an optimal CD response for each of said plurality of CD actuators; and
   using said optimal CD responses for said plurality of CD actuators which minimize the Frobenius norm of said CD modeling error as the estimated CD responses for said plurality of CD actuators.

9. A method as claimed in claim 1 further comprising the step of removing variations that are not associated with actuator responses from said estimated CD responses for said plurality of CD actuators.

10. A method as claimed in claim 9 wherein said step of removing variations that are not associated with actuator responses comprises the step of smoothing said estimated CD responses for said CD actuators.

11. A method as claimed in claim 9 further comprising the steps of:
   selecting one of said CD responses as an initial reference response;
   shifting all remaining CD responses in the cross machine direction into alignment with said initial reference response to determine relative CD response locations and define a group of overlapping CD responses;
   determining a mean response from said group of overlapping CD responses;
   shifting said CD responses in the cross machine direction into alignment with said mean response to determine new relative CD response locations and define a new group of overlapping CD responses;
   determining a new mean response from said new group of overlapping CD responses;
   repeating the steps of shifting said CD responses in the cross machine direction into alignment with said mean response and determining a new mean response until said new mean response converges within a selected tolerance to form a converged new mean response;
   using said converged new mean response as said mean response;
   setting variation bounds above and below said mean response;
   generating a family of probable CD responses within said variation bounds;
   selecting an optimal gain and a most probable response from said family of probable responses for each CD actuator response; and
   replacing the CD response for each CD actuator with the most probable response multiplied by said optimal gain and shifted in the cross machine direction by an appropriate amount for each CD actuator.

12. A method as claimed in claim 11 further comprising the steps of:
   determining CD response boundaries of all CD responses beyond which boundaries the magnitudes of said mean response consistently become smaller than a specified percentage of a maximum of said mean response; and
   replacing said CD responses outside said boundaries with zero.

13. A method as claimed in claim 11 wherein said step of setting variation bounds is performed by setting variation bounds according to a specified confidence level.

14. A method as claimed in claim 11 wherein said step of setting variation bounds is performed by setting variation bounds according to a multiple of a standard deviation of all CD responses.

15. A method as claimed in claim 11 wherein said step of generating a family of probable CD responses within said variation bounds comprises stretching or compressing said mean response with spline-interpolation.

16. A method for refining a plurality of cross-machine direction (CD) responses for a corresponding plurality of CD actuators extending across the width of a machine used for manufacturing a web of sheet material, said method comprising the steps of:
   selecting one of said CD responses as an initial reference response;
   shifting all remaining CD responses in the cross machine direction into alignment with said initial reference response to determine relative CD response locations and define a group of overlapping CD responses;
   determining a mean response from said group of overlapping CD responses;
   shifting said CD responses in the cross machine direction into alignment with said mean response to determine new relative CD response locations and define a new group of overlapping CD responses;
   determining a new mean response from said new group of overlapping CD responses;
   repeating the steps of shifting said CD responses in the cross machine direction into alignment with said mean response and determining a new mean response until said new mean response converges within a selected tolerance to form a converged new mean response;

using said converged new mean response as said mean response;

setting variation bounds above and below said mean response;

generating a family of probable CD responses within said variation bounds;

selecting an optimal gain and a most probable response from said family of probable responses for each CD actuator response; and replacing the CD response for each CD actuator with the most probable response multiplied by said optimal gain and shifted by an appropriate amount for each CD actuator.

17. A method as claimed in claim 16 further comprising the steps of:

determining CD response boundaries of all CD responses beyond which boundaries the magnitudes of said mean response consistently become smaller than a specified percentage of a maximum of said mean response; and replacing said CD responses outside said boundaries with zero.

18. A method as claimed in claim 16 wherein said step of setting variation bounds is performed by setting variation bounds according to a specified confidence level.

19. A method as claimed in claim 16 wherein said step of setting variation bounds is performed by setting variation bounds according to a multiple of a standard deviation of all CD responses.

20. A method as claimed in claim 16 wherein said step of generating a family of probable CD responses within said variation bounds comprises stretching or compressing said mean response with spline-interpolation.

* * * * *

UNITED STATES PATENT AND TRADEMARK OFFICE
CERTIFICATE OF CORRECTION

PATENT NO.   : 6,233,495 B1
DATED        : May 15, 2001
INVENTOR(S)  : Shih-Chin Chen It is certified that error appears in the above-identified patent and that said Letters Patent is hereby corrected as shown below:

Column 6,
Line 55, "accordanc present" should read -- accordance with the present --.

Column 8,
Line 38, "staring with $\hat{g}_0$" should read -- starting with -- $\hat{g}_0$ --.

Column 9,
Line 53, "where $\hat{w}_i$ (t)" should read -- where $\overline{w}_i$ (t) --.
Line 54, "$\overline{h}_i(q^{-1})$" should read -- $\hat{h}_i(q^{-1})$ --.

Column 12,
Line 41, equation 13 "$J_i^p 32 \|\hat{g}_i(x) - bp_k(x)\|$" should read -- $J_i^p = \|\hat{g}_i(x) - bp_k(x)\|$ --.

Column 13,
Line 12, "bumptest" should read -- bump-test --.

Signed and Sealed this

Twenty-fifth Day of June, 2002

Attest:

*Attesting Officer*

JAMES E. ROGAN
*Director of the United States Patent and Trademark Office*